United States Patent
Bult et al.

(10) Patent No.: US 9,999,695 B2
(45) Date of Patent: Jun. 19, 2018

(54) MICROSPHERE COMPRISING A LANTHANIDE METAL COMPLEX

(71) Applicant: UMC Utrecht Holding B.V., Utrecht (NL)

(72) Inventors: Wouter Bult, Utrecht (NL); Johannes Franciscus Wilhelmus Nijsen, Utrecht (NL); Alfred Dirk van Het Schip, Utrecht (NL)

(73) Assignee: UMC UTRECHT HOLDINGS B.V. (NL)

( * ) Notice: Subject to any disclaimer, the term of this patent is extended or adjusted under 35 U.S.C. 154(b) by 103 days.

(21) Appl. No.: 15/086,665

(22) Filed: Mar. 31, 2016

(65) Prior Publication Data

US 2016/0279273 A1    Sep. 29, 2016

Related U.S. Application Data

(63) Continuation of application No. 13/882,886, filed as application No. PCT/NL2011/050754 on Nov. 4, 2011, now Pat. No. 9,334,298.

(30) Foreign Application Priority Data

Nov. 5, 2010   (EP) .................................... 10190254

(51) Int. Cl.
| | | |
|---|---|---|
| *A61K 51/12* | (2006.01) | |
| *A61K 49/08* | (2006.01) | |
| *A61K 49/18* | (2006.01) | |
| *A61K 51/02* | (2006.01) | |
| *C07F 19/00* | (2006.01) | |

(52) U.S. Cl.
CPC .......... *A61K 51/1251* (2013.01); *A61K 49/08* (2013.01); *A61K 49/1806* (2013.01); *A61K 49/1818* (2013.01); *A61K 51/02* (2013.01); *A61K 51/1234* (2013.01); *C07F 19/00* (2013.01); *Y10T 428/2982* (2015.01)

(58) Field of Classification Search
CPC combination set(s) only.
See application file for complete search history.

(56) References Cited

U.S. PATENT DOCUMENTS

| 2010/0254875 A1 | 10/2010 | Krishna et al. |
|---|---|---|
| 2010/0278737 A1 | 11/2010 | Kataoka et al. |

FOREIGN PATENT DOCUMENTS

| EP | 1431347 A1 | 6/2004 |
|---|---|---|
| EP | 1923449 A1 | 5/2008 |
| EP | 2017253 A1 | 1/2009 |
| WO | 0001024 A1 | 1/2000 |
| WO | 0044682 A1 | 8/2000 |
| WO | 2005087274 A1 | 9/2005 |
| WO | 2006063409 A1 | 6/2006 |
| WO | 2007041579 A2 | 4/2007 |
| WO | 2007093856 A1 | 8/2007 |
| WO | 2007113624 A1 | 10/2007 |
| WO | 2007145847 A2 | 12/2007 |
| WO | 2009011589 A1 | 1/2009 |

OTHER PUBLICATIONS

Bult, Wouter, et al. "Radioactive holmium acetylacetonate microspheres for interstitial microbrachytherapy: an in vitro and in vivo stability study." Pharmaceutical research 29.3 (2012): 827-836.

*Primary Examiner* — Robert S Cabral
(74) *Attorney, Agent, or Firm* — Tarolli, Sundheim, Covell & Tummino LLP

(57) ABSTRACT

The invention is directed to a method for preparing a microsphere comprising a lanthanide metal phosphate complex, a microsphere, a powder comprising a number of the microspheres, a suspension comprising the microsphere or the powder, the use of the microsphere, a method for detecting a tumor, and a therapeutic composition comprising the microsphere, the powder, or the suspension.

The invention provides a method for preparing a microsphere that comprises a lanthanide metal phosphate complex, the method comprising:

(a) providing an organic lanthanide metal complex microsphere, wherein the lanthanide metal is present in an amount of more than 20 wt. %, based on total weight of the microspheres, and wherein the organic lanthanide metal complex comprises a lanthanide ion and organic ligands with which the lanthanide ion forms the complex; and thereafter (b) replacing at least part of the organic ligands in the organic lanthanide metal complex microsphere with phosphate in a chimie douce reaction, wherein the lanthanide metal is present in the resulting microsphere in an amount of more than 20 wt. %, based on total weight of the microsphere, and wherein the lanthanide metal complex in the resulting microsphere comprises a lanthanide ion and phosphate.

36 Claims, No Drawings

MICROSPHERE COMPRISING A LANTHANIDE METAL COMPLEX

RELATED APPLICATIONS

The present application is a Continuation of U.S. Ser. No. 13/882,886, filed on Jul. 10, 2013, which is a U.S. National Stage under 35 USC 371 patent application, claiming priority to Serial No. PCT/NL2011/050754, filed on Nov. 4, 2011, which claims priority from EP 10190254.2, filed on Nov. 5, 2010, all of which are incorporated herein by reference.

FIELD OF THE INVENTION

The invention is directed to a method for preparing a microsphere comprising a lanthanide metal phosphate complex, a microsphere, a powder comprising a number of the microspheres, a suspension comprising the microsphere or the powder, the use of the microsphere, a method for detecting a tumour, and a therapeutic composition comprising the microsphere, the powder, or the suspension.

BACKGROUND OF THE INVENTION

Radioactive holmium-166 loaded poly-(L)-lactic acid (PLLA) microspheres have been proposed as a promising new treatment for liver malignancies in the early 1990's (Mumper et al., *J. Nucl. Med.* 1991, 32, 2139-2143). Since then these microspheres have been studied extensively (Nijsen et al., *Eur. J. Nucl. Med.* 1999, 26, 699-704; Nijsen et al., *Biomaterials* 2001, 22 3073-3081; Zielhuis et al., *Biomaterials* 2005, 26, 925-932; and Zielhuis et al., *Biomacromolecules* 2006, 7, 2217-2223). $^{166}$Ho (166-holmium) is a combined beta and gamma emitter. These radioactive microspheres have superior physical and chemical properties than the currently available $^{90}$Y (90-yttrium) microspheres (Murthy et al., *Radiographics* 2005, 25 *Suppl.* 1, S41-S55). The holmium loaded microspheres can, for instance, be imaged directly using nuclear imaging, due to the gamma radiation that $^{166}$Ho emits, and MR imaging, due to the high paramagnetic value (x value) of holmium.

The holmium loaded PLLA (poly-(L-lactic acid)) microspheres can be prepared by incorporating holmium acetylacetonate into poly(L)-lactic acid by way of solvent evaporation. The stability of the microspheres so obtained is believed to be the result of the interaction of the carbonyl groups of poly-(L)-lactic acid with the Ho-ion in the holmium acetylacetonate complex (Nijsen et al., *Biomaterials* 2001, 22 3073-3081). The poly-(L)-lactic acid thus functions as a binder or stabiliser for the formation of the microspheres.

A disadvantage to holmium loaded PLLA microspheres is the limited loading capacity of these microspheres. The average holmium loading of these microspheres is around 17 wt. % (w/w) (Nijsen et al., *Biomaterials* 2001, 22 3073-3081 and Zielhuis et al., *Biomaterials* 2005, 26, 925-932).

Microspheres with substantially higher content of lanthanide metal are disclosed in WO-A-2009/011589. In accordance with the invention disclosed therein the microspheres with high lanthanide metal content are prepared using a lanthanide metal organic compound, while no binder or only very small amounts of binder such as poly-(L)-lactic acid is used. The lanthanide ions form a complex with a number of organic molecules, such as acetylacetonate, 3,5-heptanedione, and/or 2-(acetoacetoxyethyl)methacrylate. The invention of WO-A-2009/011589 shows that the reduction of binder material does not lead to a disintegration of the microspheres. Instead, the resulting microspheres are highly stable and contain a high amount of lanthanide while no (or hardly any) binder is needed. Accordingly, microspheres having a lanthanide metal content of more than 20 wt. %, based on total microsphere, can be prepared. These microspheres have a number of advantages, including a shorter neutron activation time and higher specific activity. This in turn leads to a reduced amount of microspheres to be administered to patients and improved MRI (magnetic resonance imaging) signals.

It would, however, be desirable to design microspheres wherein the ligands complexing with the lanthanide metal are based on compounds naturally occurring in the body, so that, when applied to a patient, possible toxic effects of the microspheres are minimized.

Objective of the invention is to meet this existing need in the art and provide improved lanthanide metal microspheres.

The inventors found that this objective can, at least in part, be met by providing lanthanide metal nanospheres or microspheres wherein the lanthanide is present in a specific different complex.

SUMMARY OF THE INVENTION

In a first aspect, the invention is directed to a method for preparing a microsphere that comprises a lanthanide metal phosphate complex, the method comprising (a) providing an organic lanthanide metal complex microsphere, wherein the lanthanide metal is present in an amount of more than 20 wt. %, based on total weight of the microspheres, and wherein the organic lanthanide metal complex comprises a lanthanide ion and organic ligands with which the lanthanide ion forms the complex; and thereafter (b) replacing at least part of the organic ligands in the organic lanthanide metal complex microsphere with phosphate in a chimie douce reaction, wherein the lanthanide metal is present in the resulting microsphere in an amount of more than 20 wt. %, based on total weight of the microsphere, and wherein the lanthanide metal complex in the resulting microsphere comprises a lanthanide ion and phosphate.

Organic ligand originally present in the organic lanthanide metal complex microsp here is replaced in the method of the invention with phosphate according to a chimie douce (soft chemistry) reaction, more particularly in an ion exchange chimie douce reaction. Chimie douce reactions (Rouxel et al., *Solid State Ionics* 1996, 84, 141-149) are topotactic, meaning that its products retain a memory of the precursor geometry. The exchange of the original organic ligand for phosphate does not (or hardly) affect the structure and geometry of the original organic lanthanide metal complex microsphere. Hence, the final microsphere with phosphate ligands has essentially the same structure and geometry as the original organic lanthanide metal complex microsphere. Usually, chimie douce reactions take place under mild conditions, which is advantageous when organic compounds are involved.

The inventors surprisingly found that when organic ligand is replaced for phosphate, the stability of the lanthanide metal microspheres is further improved.

Furthermore, a skilled person seeking lanthanide metal phosphate complex microspheres would intuitively not first prepare a microsphere with another ligand, but directly start with a phosphate starting material. It is not obvious to first prepare microspheres that lack phosphate and only then introduce phosphate. However, by doing so lanthanide metal phosphate complex microspheres with unique structure and properties are obtained.

The chimie douce reaction of step (b) above typically involves suspending the organic lanthanide metal complex microsphere of step (a) in a phosphate buffer. The chimie douce reaction typically occurs at a temperature of 100° C. or less, such as 90° C. or less. The phosphate buffer, can for instance be a phosphate buffer at pH of 5.0-10.0, such as at pH 7.0-8.0, pH 7.2-7.6, or at pH of about 7.4. The phosphate concentration of the buffer can be 100 mM or more. The upper limit of the phosphate concentration is not critical. It is expected that the reaction goes faster at higher phosphate concentrations, such as 200 mM or more, or 500 mM or more. The chimie douce reaction can be performed for 5 hours or more, such as 10 hours or more, or 24 hours or more. This will at least partially result in an exchange of the organic compound with phosphate. The reaction may be completed within 10 days or less, such as 6 days or less, or even 4 days or less.

The organic lanthanide metal complex starting material can be prepared as described in WO-A-2009/011589, i.e. by
dissolving a lanthanide metal organic compound in an organic solvent
emulsifying the organic phase in an aqueous solution comprising an emulsifier;
stirring, and optionally heating, the emulsion so obtained so as to reduce the volume of the emulsion by evaporating at least part of the organic solvent, thereby obtaining a mixture; and
recovering from the mixture so obtained the organic lanthanide metal complex microsphere.

Advantageously, organic ligand is a betadicarbonyl compound that exhibit keto-enol tautomerism, such as acetylacetonate, 2,4-heptanedione or 2-(acetoacetoxyethyl)-methacrylate. These ligands allows the preparation of microspheres with high lanthanide content and improved stability. This high lanthanide content and improved stability are a result of the structure of the microsphere, which is retained when exchanging organic ligand for phosphate.

The organic lanthanide metal complex microsphere starting material is preferably free or substantially free of a binder material such as poly(L-lactic acid). The amount of binder material can, for example, be less than 1 wt. %, based on total weight of the microsphere. In the context of this application, a binder is defined as a polymer matrix into which the metal complex can be incorporated, whereby the binder serves to stabilise and form the microsphere.

Since the final microsphere with phosphate ligands has essentially the same structure and geometry as the original organic lanthanide metal complex microsphere, the invention is further directed to a microsphere obtainable by the method of the invention. This method provides phosphate lanthanide metal complex microspheres with unique structures and geometries that are derived from different organic ligands.

DETAILED DESCRIPTION OF THE INVENTION

In a preferred embodiment, after replacing at least part of the organic ligands in the organic lanthanide metal complex microsphere with phosphate in a chimie douce reaction, the amount of original organic ligand in the resulting microsphere is 20 wt. % or less based on total weight of the microsphere, such as 10 wt. % or less, preferably 5 wt. % or less, or 1 wt. % or less. Most preferably, essentially all of the original organic ligand has been replaced by phosphate.

The invention provides a microsphere comprising a lanthanide metal phosphate complex wherein the lanthanide metal is present in an amount of more than 20 wt. %, based on total weight of the microsphere, and wherein the lanthanide metal complex comprises a lanthanide ion and phosphate.

Lanthanide phosphates are known as slightly soluble salts (Kijkowska et al., *Key Engineering Materials* 2005, 284-286, 79-82). These phosphates can be obtained by precipitation from aqueous solutions of their salts. However, this approach does not result in formation of microspheres, and more in particular not in the formation of microspheres with predefined characteristics (in particular size, sphericity, surface roughness and stability). The inventors surprisingly found that the microspheres of the invention have excellent sphericity, stability and have a smooth surface. Furthermore, the size can be adapted.

In accordance with the invention, any of the lanthanide metals can be used. Suitably, the lanthanide metal comprises one or more selected from the group consisting of holmium, gadolinium, dysprosium, lutetium, samarium or yttrium. Preferably, the lanthanide metal comprises holmium, lutetium, gadolinium or yttrium. More preferably, the lanthanide metal is holmium or yttrium. Most preferably, the lanthanide metal is holmium.

Suitably the lanthanide metal to be used in accordance with the invention is present in an amount of more than 22 wt. %, based on total weight of the microsphere. The lanthanide can preferably be present in the microsphere in an amount in the range of 25-70 wt. %, based on total weight of the microsphere. When the lanthanide metal is yttrium, the lanthanide is preferably present in an amount in the range of 22-45 wt. %, more preferably in the range of from 25-40 wt. %, based on total weight of the microsphere. When the lanthanide metal is not yttrium it is preferably present in an amount in the range of 30-70 wt. %, based on total weight of the microsphere, preferably in the range of 40-65 wt. %, such as in the range of 50-60 wt. %

The difference between the amounts to be used in case the lanthanide metal is yttrium or the lanthanide metal is another type of lanthanide metal is due to the difference between the respective atomic mass of yttrium and the respective other lanthanide metals.

Preferably, the microsphere of the invention has an atomic phosphor content of 3 wt. % or more, such as 5 wt. % or more, or even 10 wt. % or more, based on total weight of the microsphere. Due to the difference between the respective atomic mass of yttrium and the respective other lanthanides the atomic phosphor content of microspheres wherein the lanthanide metal is yttrium can be as high as 14.1 wt. %, while the atomic phosphor content of microspheres wherein the lanthanide metal is not yttrium can be as high as 11 wt. %.

The microsphere of the invention can optionally comprise an organic ligand. This organic ligand can suitably belong to the betadicarbonyl compounds that exhibit the keto-enol tautomerism, such as acetylacetonate, 2,4-heptanedione and 2-(acetoacetoxyethyl)-methacrylate. Preferably, the optional organic ligand is acetylacetonate. When present, the organic ligand is preferably present in the microsphere in an amount of 20 wt. % or less based on total weight of the microsphere, such as 10 wt. % or less, more preferably 5 wt. % or less, or 1 wt. % or less.

The microsphere of the invention preferably has a diameter in the range of 20 nm to 300 µm. In a particular embodiment of the invention, the microsphere has a diameter in the range of 20-200 nm. Such microspheres can attractively be used as local therapeutic and in addition for diagnostic purposes. For local therapeutic purposes the microsphere(s) can suitably be delivered locally, for instance, via a catheter or via direct injection, whereas for diagnostic purposes the microsphere(s) can be introduced into the body of an individual via parenteral administration, e.g. via injection, infusion, etc. In a further embodiment, the microsphere according to the invention has a diameter in the range of 1-10 µm, such as in the range of 3-5 µm. In a further embodiment, the microsphere according to the invention has a diameter in the range of 10-200 µm, such as in the range of 20-50 µm.

In a further aspect, the invention is directed to a powder comprising a number of microspheres as defined herein.

The microspheres in the powder preferably have an average sphericity, S, of more than 0.90. More preferably the sphericity, S, of the microspheres in the powder of the invention is more than 0.92, even more preferably more than 0.95, and most preferably more than 0.97. The sphericity, S, is defined by the following equation $$S = \frac{4\pi A}{P^2},$$

wherein
A is the projected area of the microsphere in a microscopic image; and
P is the perimeter of the microsphere in a microscopic image.

The average sphericity of the powder can, for instance, be determined by inputting images of microspheres obtained through the use of a microscope (such as a scanning electron microscope) and the like in an image-analysis device. Specifically the projected area A and the perimeter P of each microspheres can be determined on the basis of the micrographs thus obtained. For example, arbitrarily selected 200 microspheres can be inspected for the sphericities according to the foregoing method and the results are averaged and the resulting average value is defined to be the average sphericity of the powder.

In an embodiment, the microsphere according to the invention has been made radioactive. Radioactive microspheres contain a radioactive element that emits radiation suitable for diagnosis and/or therapy. The radionuclides are (rapidly) decaying (half-life of a few minutes to a few weeks) to, in general, a stable nuclide after emitting ionising radiation. The most common types of ionising radiation are (i) alpha particles, (ii) beta particles, i.e. electrons that are emitted from the atomic nucleus, and (iii) gamma-rays ($\gamma$) and X-rays. For therapeutic purposes, radionuclides that emit beta ($\beta$) or electron radiation, and in some exceptional applications alpha ($\alpha$) radiation, are applied. The $\beta$ radiation will damage DNA in the cell which results in cell death.

Preferably, the microspheres according to the invention essentially maintain its/their structure during neutron activation.

Nuclear imaging is extremely sensitive to abnormalities in organ structure or function. The radioactive diagnostic compounds can identify abnormalities early in the progression of a disease, long before clinical problems become manifest. Moreover, radiopharmaceuticals comprise the unique ability that they can provide a treatment option by exchanging the diagnostic nuclide for a therapeutic one but using the same carrier. In most of the lanthanides only the radioactivity of the radiopharmaceutical has to be increased as these radionuclides emit often both $\gamma$ and $\beta$ radiation for diagnosis and therapy, respectively. The distribution and biological half-life of the specific therapeutic compound are then mostly very similar to that of the diagnostic compound. For example the use of $^{166}$Ho microspheres for diagnostic application in a screening dose will contain typically 100-500 MBq and for treatment of different types of tumors, e.g. hepatocellular carcinoma (HCC), liver metastases, a dose of up to 16 GBq.

In a further aspect, therefore, the invention is directed to a therapeutic composition which comprises a radioactive microsphere or a radioactive powder according to the invention. Such a therapeutic composition can suitably be brought in the form of a suspension before it is administered to an individual.

Since the microspheres of the invention have a substantial higher amount of holmium compared to holmium loaded PLLA microspheres (Nijsen et al., *Eur. J. Nucl. Med.* 1999, 26, 699-704; Nijsen et al., *Biomaterials* 2001, 22, 3073-3081; Nijsen et al., *Biomaterials* 2002, 23, 1831-1839; Zielhuis et al., *Biomaterials* 2005, 26, 925-932; and Zielhuis et al., *Biomacromolecules* 2006, 7, 2217-2223) and the holmium loaded acetylacetonate microspheres disclosed in WO-A-2009/011589 the therapeutic compositions of the microspheres of the invention have the advantage that they require a shorter neutron activation time and that they display a higher specific activity. In addition, a reduced amount of microspheres need to be administered to patients.

Said microsphere of the present invention can be directly generated using a radioactive component, such as radioactive holmium. Preferably however, a non-radioactive microsphere of the invention is firstly generated, followed by neutron-irradiation of said microsphere which decreases unnecessary exposure to radiation of personnel. This can avoid the use of high doses of radioactive components and the need for specially equipped (expensive) facilities, such as hot cells and transport facilities.

The microsphere of the invention can be used for visualisation of benign lesions in Tuberous Sclerosis by MRI. The microspheres are used without rendering them more radioactive by means of neutron irradiation.

In yet a further aspect, the invention is directed to a suspension comprising a microsphere or a powder in accordance with the invention.

The suspension of the invention suitably comprises a scanning suspension, whereby the microsphere(s) is (are) capable of at least in part disturbing a magnetic field. Said microsphere(s) can be detected by a non-radioactive scanning method such as magnetic resonance imaging (MRI). Preferably said scanning suspension comprises an MRI scanning suspension or a nuclear scanning suspension.

Magnetic resonance imaging (MRI) provides information of the internal status of an individual. A contrast agent is often used in order to be capable of obtaining a scanning image. For instance, ferrite particles and gadolinium-DTPA (diethylaminetriaminepentaacetic acid) complexes are often used in contrast agents for MRI scanning. This way, a good impression can be obtained of internal disorders, like the presence of (a) tumour(s).

After diagnosis, a treatment is often started involving administration of a pharmaceutical composition to a patient. It is often important to monitor the status of a patient during treatment as well. For instance the course of a treatment and targeting of a drug can be monitored, as well as possible side effects which may imply a need for terminating, or temporarily interrupting, a certain treatment.

Sometimes local treatment in only a specific part of the body is preferred. For instance, tumour growth can sometimes be counteracted by internal radiotherapy comprising administration of radioactive microspheres to an individual. If said radioactive microspheres accumulate inside and/or around the tumour, specific local treatment is possible.

The invention also relates to the use of a microsp here in accordance with the invention for the preparation of a scanning suspension. Preferably, the scanning image obtained by using the microsphere or powder is a magnetic resonance scanning image or a nuclear scanning image. In this application the meaning of the word suspension has to be understood as at least including dispersions.

A scanning suspension of the invention can be used for determining a flowing behaviour of a microsphere.

A scanning suspension of the invention can also be used for detecting a site of angiogenesis. A site of angiogenesis can be detected by determining the flowing behaviour of the microsphere(s) according to the invention. Typically, the microsphere has a diameter of about 3-5 µm for such an application.

Hence, the invention also provides the use of the microsphere according to the invention for detecting a site of angiogenesis.

A scanning suspension of the invention is also very suitable for detecting a malignancy, e.g. a tumour. Preferably, said tumour comprises a liver metastasis.

Therefore, the invention also provides the use of a microsphere according to the invention for detecting a malignancy, such as a tumour. Such a tumour can be detected without the need of using radioactive material. Alternatively, microspheres with low radioactivity can be used. After a tumour has been detected, the tumour can be treated with a therapeutic composition according to the invention comprising the same kind of microspheres as said scanning suspension. In such a therapeutic composition, however, said microspheres are preferably rendered (more) radioactive. Despite the difference in radioactivity, the microspheres of the diagnostic composition for detecting the tumour and the microspheres of said therapeutic composition can be chemically the same.

In one aspect the invention provides a method for detecting a malignancy, e.g. a tumour, comprising
   administering to an individual a scanning suspension comprising a microsphere in accordance with the invention which is capable of at least in part disturbing a magnetic field;
   obtaining a scanning image; and
   determining whether said image reveals the presence of a tumour.

In another attractive embodiment of the invention, a microsphere of the invention has a diameter in the range of 15-200 µm, more specifically in the range of 15-100 µm, even more specifically in the range of 20-100 µm, and most preferably in the range of 20-50 µm or in the range of from 80-100 µm. A microsphere of such sizes is very suitable for radiotherapeutic purposes. Such a microsphere comprises a diameter sufficiently large to enable said microsphere to be lodged within arterioles. The invention also relates to the use of a microsphere according to the invention, wherein the microsphere has a diameter in the range of from 20-100 µm, for embolising a blood vessel. In using relatively large microspheres, for example in the range of from 50-200 µm, embolisation of tumours, for example bone cancer and tumours due to Tuberous Sclerosis, is possible. When use is made of microspheres having a diameter in the range of from 50-200 µm, embolisation of the vessels leading to said tumour may lead to retardation of tumour growth.

As will be clear from the above, the size of the microsphere in accordance with the invention may vary considerably, depending on the particular use intended. The skilled person will understand that the desired microsphere size can be obtained by adjusting the relevant process conditions in the preparation process conditions as described above, such as the conditions of the solvent evaporation process.

In another embodiment of the invention, a microsphere of the invention is administered to a complex of interest.

Preferably, such a complex of interest comprises a complex with a desired function which it can perform within an organism.

More preferably, such a complex of interest comprises an organelle or cell of an organism. Most preferably, such a complex of interest comprises a liposome or a white blood cell. After administration of a microsphere of the invention to such a complex of interest, the complex of interest can be detected by a scanning method such as MRI. This way a presence and/or migration of the complex of interest can be detected. For instance, a liposome is useful for delivering a nucleic acid of interest to a suitable site for gene therapy. If such liposome has been provided with a microsphere of the invention it can be determined where said liposome is present inside an organism. It can then be estimated whether a nucleic acid of interest is delivered to a desired site. As another example, after administration of a microsphere of the invention to a white blood cell, migration of said white blood cell to a site of inflammation, or to a tumour, can be detected using a scanning method such as MRI.

The invention thus also provides the use of a microsphere of the invention for detecting a presence and/or migration of a complex of interest.

It will be clear from the above that the suspension according to the invention can be used as such as a therapeutic composition and/or diagnostic composition. In addition, said suspension can be used for the preparation of a diagnostic composition.

Preferably, such a suspension is essentially non-radioactive.

Preferably, the present microsphere is biodegradable, allowing for degradation in an animal body after it has been used, for instance for radiotherapy and/or MRI.

In addition, the invention provides the use of a microsphere of the invention for the preparation of a radioactive therapeutic composition. In addition, the invention provides the use of a microsphere according to the invention for the preparation of a diagnostic composition.

The term "individual" as used in this application is meant to refer to an animal, preferably a human.

Preferably, the microsphere in accordance with the invention is paramagnetic, for instance comprising holmium, gadolinium and/or dysprosium.

The invention further provides a method for treating an individual suffering from a malignancy, e.g. a tumour, comprising:
   administering to said individual a scanning suspension comprising a microsphere which is capable of at least in part disturbing a magnetic field;
   obtaining a scanning image of the individual;
   determining the distribution of the microsphere within the individual;
   administering to the individual a therapeutic composition comprising the microsphere.

The microsphere in the therapeutic composition is more radioactive than the microsphere in the scanning suspension.

The radioactive therapeutic composition according to the invention is particularly suitable for treatment of a liver tumour, for instance a liver metastasis.

Of course, other kind of tumours can also be treated by embolising a blood vessel by a microsphere of the invention or by direct injection in the tumour known as interstitial microbrachytherapy.

The invention furthermore provides a method for preparing a therapeutic composition for treatment of a malignancy, e.g. a tumour, comprising the steps of:
- in a first step obtaining a scanning image, more specifically an MRI or nuclear image of a person provided with a scanning suspension of the invention;
- in a second step preparing a therapeutic suspension for treatment of a tumour, using microspheres with essentially the same chemical structure as the microspheres in the scanning suspension, which microspheres are made more radioactive than the microspheres in the scanning suspension.

In one embodiment of the invention an amount of microspheres is prepared prior to obtaining said scanning image, wherein a first part of said amount of microspheres is used for preparing the scanning suspension and a second part of the amount of microspheres is used for preparing the therapeutic suspension.

The invention further provides a method for obtaining a scanning image, comprising administering a scanning suspension to an individual and subsequently generating a scanning image of the individual, wherein the scanning suspension comprises a scanning suspension in accordance with the invention.

The invention claimed is:

1. A microsphere comprising a lanthanide metal phosphate complex obtainable by a method comprising:
   (a) providing an organic lanthanide metal complex microsphere, wherein the lanthanide metal is present in an amount of more than 20 wt. %, based on total weight of the microspheres, wherein the organic lanthanide metal complex comprises a lanthanide ion and organic ligands with which the lanthanide ion forms the complex, and wherein the amount of binder in the organic lanthanide metal complex microsphere is less than 1 wt. % based on the total weight of the microspheres; and thereafter
   (b) replacing at least part of the organic ligands in the organic lanthanide metal complex microsphere with phosphate in a chimie douce reaction,
   wherein the lanthanide metal is present in the resulting microsphere in an amount of more than 20 wt. %, based on total weight of the microsphere, and wherein the lanthanide metal complex in the resulting microsphere comprises a lanthanide ion and phosphate, and wherein the diameter of the microsphere ranges from about 200 nm to about 300 μm.

2. A microsphere comprising a lanthanide metal phosphate complex wherein the lanthanide metal is present in an amount of more than 20 wt. %, based on total weight of the microsphere; wherein the lanthanide metal complex comprises a lanthanide ion and phosphate; and wherein the microsphere has a diameter in the range of from about 200 nm to about 300 μm.

3. A microsphere according to claim 2, having an organic ligand content of 20 wt. % or less.

4. A microsphere according to claim 2, wherein the microsphere has an atomic phosphor content of 3 wt. % or more, based on total weight of the microsphere.

5. A microsphere according to claim 2, having a lanthanide metal content in the range of 22-70 wt. % based on total weight of the microsphere.

6. A microsphere according to claim 2, wherein
   the lanthanide metal is yttrium, and wherein the microsphere has an yttrium content in the range of 22-45 wt. %, based on total weight of the microsphere; or
   the lanthanide metal is not yttrium, and wherein the microsphere has a lanthanide content in the range of 30-70 wt. %, based on total weight of the microsphere.

7. A microsphere according to claim 2, wherein the lanthanide metal comprises one or more from the group consisting of yttrium, holmium, gadolinium, dysprosium, lutetium, and samarium.

8. A microsphere according to claim 2, wherein the microsphere has a diameter in the range of about 1 μm to about 300 μm.

9. A microsphere according to claim 2, wherein the microsphere has been made radioactive.

10. A powder comprising a number of microspheres as defined in claim 2.

11. A powder according to claim 10, wherein said microspheres have an average sphericity, S, of more than 0.90, wherein the sphericity, S, is defined by $$S = \frac{4\pi A}{P^2},$$

wherein
A is the projected area of the microsphere in a microscopic image; and
P is the perimeter of the microsphere in a microscopic image.

12. A suspension comprising the microsphere according to claim 2, said suspension being at least one of a therapeutic suspension, an MRI scanning suspension, and a nuclear scanning suspension.

13. A method of at least one of detecting and treating a malignancy comprising administering to an individual a microsphere according to claim 2, wherein said malignancy comprises a liver metastasis.

14. A method for detecting a tumour, comprising:
   administering to an individual a scanning suspension according to claim 12;
   obtaining a scanning image; and
   determining whether said image reveals the presence of a tumour.

15. A therapeutic composition comprising a microsphere according to claim 2, wherein the microsphere(s) is(are) radioactive.

16. A suspension comprising the powder of claim 10, the suspension being at least one of a therapeutic suspension, an MRI scanning suspension, and a nuclear scanning suspension.

17. A method of at least one of detecting and treating a malignancy comprising administering to an individual a powder according to claim 10, wherein said malignancy comprises a liver metastasis.

18. A method of at least one of detecting and treating a malignancy comprising administering to an individual a suspension according to claim 12, wherein said malignancy comprises a liver metastasis.

19. A therapeutic composition comprising a powder according to claim 10, wherein the microsphere(s) is (are) radioactive.

20. A therapeutic composition comprising a suspension according to claim 12, wherein the microsphere(s) is (are) radioactive.

21. A microsphere according to claim 2, having a lanthanide metal content in the range of 25-70 wt. % based on total weight of the microsphere.

22. A microsphere according to claim 2, having a lanthanide metal content in the range of 22-45 wt. % based on total weight of the microsphere.

23. A microsphere according to claim 2, having a lanthanide metal content in the range of 25-40 wt. % based on total weight of the microsphere.

24. A microsphere according to claim 2, having a lanthanide metal content in the range of 30-70 wt. % based on total weight of the microsphere.

25. A microsphere according to claim 2, having a lanthanide metal content in the range of 40-65 wt. % based on total weight of the microsphere.

26. A microsphere according to claim 2, having a lanthanide metal content in the range of 50-60 wt. % based on total weight of the microsphere.

27. A microsphere according to claim 2, wherein the diameter of the microsphere ranges from about 1 μm to about 300 μm.

28. A microsphere according to claim 2, wherein the diameter of the microsphere ranges from about 1 μm to about 10 μm.

29. A microsphere according to claim 2, wherein the diameter of the microsphere ranges from about 3 μm to about 5 μm.

30. A microsphere according to claim 2, wherein the diameter of the microsphere ranges from about 10 μm to about 200 μm.

31. A microsphere according to claim 2, wherein the diameter of the microsphere ranges from about 20 μm to about 50 μm.

32. A powder according to claim 11, wherein said microspheres have an average sphericity, s, of more than 0.92.

33. A powder according to claim 11, wherein said microspheres have an average sphericity, s, of more than 0.95.

34. A powder according to claim 11, wherein said microspheres have an average sphericity, s, of more than 0.97.

35. A method according to claim 17, wherein the powder is made radioactive.

36. A method according to claim 18, wherein the suspension has been made radioactive.

* * * * *